(12) United States Patent
Stigall

(10) Patent No.: US 11,006,840 B2
(45) Date of Patent: May 18, 2021

(54) DEVICE, SYSTEM, AND METHOD FOR ASSESSING INTRAVASCULAR PRESSURE

(71) Applicant: Volcano Corporation, San Diego, CA (US)

(72) Inventor: Jeremy Stigall, Carlsbad, CA (US)

(73) Assignee: PHILIPS IMAGE GUIDED THERAPY CORPORATION, San Diego, CA (US)

(*) Notice: Subject to any disclaimer, the term of this patent is extended or adjusted under 35 U.S.C. 154(b) by 972 days.

(21) Appl. No.: 14/562,436

(22) Filed: Dec. 5, 2014

(65) Prior Publication Data

US 2015/0157215 A1 Jun. 11, 2015

Related U.S. Application Data

(60) Provisional application No. 61/913,160, filed on Dec. 6, 2013.

(51) Int. Cl.
*A61B 5/02* (2006.01)
*A61B 5/0215* (2006.01)
*A61B 5/00* (2006.01)
*A61B 8/12* (2006.01)
*A61B 5/026* (2006.01)
*A61B 8/06* (2006.01)

(52) U.S. Cl.
CPC ........ *A61B 5/02007* (2013.01); *A61B 5/0215* (2013.01); *A61B 5/02158* (2013.01); *A61B 5/6858* (2013.01); *A61B 5/6876* (2013.01); *A61B 5/6886* (2013.01); *A61B 5/026* (2013.01); *A61B 8/06* (2013.01); *A61B 8/12* (2013.01); *A61B 2562/222* (2013.01)

(58) Field of Classification Search
CPC . A61B 5/02007; A61B 5/6858; A61B 5/6876; A61B 5/6886; A61B 5/02158; A61B 5/0215; A61B 8/06; A61B 8/12; A61B 2562/222; A61B 5/026
See application file for complete search history.

(56) References Cited

U.S. PATENT DOCUMENTS 4,497,324 A 2/1985 Sullivan
4,559,951 A * 12/1985 Dahl .................... A61B 5/0422
600/374

(Continued)

FOREIGN PATENT DOCUMENTS

JP 09140802 A * 6/1997
WO 2011069505 A1 6/2011

OTHER PUBLICATIONS

International Search Report and Written Opinion received in Patent Cooperation Treaty Application No. PCT/US2014/068874, dated Mar. 26, 2015, 12 pages.

*Primary Examiner* — Jacqueline Cheng
*Assistant Examiner* — Tho Q Tran

(57) ABSTRACT

What is described is an apparatus for intravascular pressure measurement, comprising an elongate body, a first pressure sensor and a centering assembly disposed adjacent the sensor. In one aspect, the elongate body has a uniform diameter from the distal end to the proximal end. In another aspect, the uniform diameter is 0.035 inches or less. In still a further aspect, the elongated body is a catheter having a plurality of reinforcing filaments and the filaments are utilized to electrically connect the sensor to the proximal end.

21 Claims, 4 Drawing Sheets

(56) References Cited

U.S. PATENT DOCUMENTS

| | | | |
|---|---|---|---|
| 4,913,164 A * | 4/1990 | Greene | A61N 1/057 607/126 |
| 5,016,646 A * | 5/1991 | Gotthardt | A61N 1/056 607/122 |
| 5,067,491 A * | 11/1991 | Taylor, II | A61B 5/0215 600/486 |
| 5,564,425 A * | 10/1996 | Tonokura | A61B 5/02055 600/486 |
| 5,701,905 A * | 12/1997 | Esch | A61B 5/0215 600/486 |
| 6,030,371 A | 2/2000 | Pursley | |
| 6,656,153 B1 | 12/2003 | Sakai et al. | |
| 7,329,223 B1 * | 2/2008 | Ainsworth | A61B 5/0084 600/300 |
| 7,776,380 B2 | 8/2010 | Pursley | |
| 8,298,156 B2 | 10/2012 | Manstrom et al. | |
| 8,485,985 B2 | 7/2013 | Manstrom et al. | |
| 9,333,336 B2 * | 5/2016 | Victorine | H01R 43/00 |
| 2001/0014813 A1 * | 8/2001 | Saadat | A61F 2/2493 606/198 |
| 2002/0095141 A1 | 7/2002 | Belef et al. | |
| 2002/0156417 A1 * | 10/2002 | Rich | A61B 5/0215 604/65 |
| 2002/0177765 A1 * | 11/2002 | Bowe | A61B 18/1492 600/374 |
| 2004/0243057 A1 | 12/2004 | Vinten-Johansen | |
| 2005/0268724 A1 * | 12/2005 | Tenerz | A61B 5/0215 73/753 |
| 2008/0140180 A1 | 6/2008 | Dolan et al. | |
| 2008/0319278 A1 | 12/2008 | Omtveit | |
| 2009/0005675 A1 * | 1/2009 | Grunwald | A61B 8/488 600/424 |
| 2010/0241069 A1 | 9/2010 | Hatten | |
| 2010/0331813 A1 * | 12/2010 | Robinson | A61B 5/0215 604/503 |
| 2011/0092955 A1 * | 4/2011 | Purdy | A61B 5/0215 604/523 |
| 2011/0093007 A1 * | 4/2011 | Abbott | A61B 5/415 606/213 |
| 2012/0191174 A1 * | 7/2012 | Vinluan | A61F 2/07 623/1.12 |
| 2012/0220883 A1 | 8/2012 | Manstrom et al. | |
| 2013/0131523 A1 | 5/2013 | Suchecki et al. | |
| 2013/0190803 A1 | 7/2013 | Angel | |
| 2013/0289369 A1 | 10/2013 | Margolis | |
| 2013/0303914 A1 | 11/2013 | Hiltner et al. | |

* cited by examiner

DEVICE, SYSTEM, AND METHOD FOR ASSESSING INTRAVASCULAR PRESSURE

CROSS REFERENCE TO RELATED APPLICATION

The present application claims priority to and the benefit of U.S. Provisional Patent Application No. 61/913,160 filed Dec. 6, 2013, which is hereby incorporated by reference herein in its entirety.

TECHNICAL FIELD

Embodiments of the present disclosure relate generally to the field of medical devices and, more particularly, to a device, system, and method for assessing pressure within vessels. In particular, the present disclosure relates to the assessment of the severity of a blockage or other restriction to the flow of fluid through a vessel. Aspects of the present disclosure are particularly suited for evaluation of biological vessels in some instances. For example, some particular embodiments of the present disclosure are specifically configured for the evaluation of a stenosis of a human blood vessel.

BACKGROUND

Heart disease is a serious health condition affecting millions of people worldwide. One major cause of heart disease is the presence of blockages or lesions within the blood vessels that reduce blood flow through the vessels. Traditionally, surgeons have relied on X-ray fluoroscopic (planar) images to show the external shape or silhouette of the blood vessels to guide treatment. Unfortunately, using only X-ray fluoroscopic images lends a great deal of uncertainty about the exact extent and orientation of the lesion responsible for the occlusion, making it difficult to find the exact location of the stenosis for treatment. In addition, X-ray fluoroscopy is an inadequate reassessment tool to evaluate the vessel after surgical treatment.

A currently accepted technique for assessing the severity of a stenosis in a blood vessel, including ischemia-causing lesions, is fractional flow reserve (FFR). FFR is defined as the ratio of the maximal blood flow in a stenotic artery, taken distal to the lesion, to normal maximal flow. Accordingly, to calculate the FFR for a given stenosis, two blood pressure measurements are taken: one measurement distal or downstream to the stenosis and one measurement proximal or upstream to the stenosis. FFR is a calculation of the ratio of the distal pressure measurement relative to the proximal pressure measurement. FFR provides an index of stenosis severity that allows determination as to whether the blockage limits blood flow within the vessel to an extent that treatment is required. The more restrictive the stenosis, the greater the pressure drop across the stenosis, and the lower the resulting FFR. FFR measurements can be used as a decision point for guiding treatment decisions. The normal value of FFR in a healthy vessel is 1.00, while values less than about 0.80 are generally deemed significant and require treatment. Common treatment options include angioplasty, atherectomy, and stenting.

One method of measuring the pressure gradient across a lesion is to use a pressure sensing guidewire that has a pressure sensor embedded within the guidewire itself. A user may initially position the pressure sensor of the guidewire distal to the lesion and measure the distal pressure before drawing the guidewire backwards to reposition the sensor proximal to the lesion to measure the proximal pressure. This method has the disadvantages of inaccurate pressure readings due to drift and increased susceptibility to thermal variations, difficulty maneuvering a guidewire through blockages, high manufacturing costs, and time-consuming repositioning steps (especially in situations involving multiple lesions). Further, pressure-sensing guidewires often suffer from reduced precision and accuracy in making intravascular pressure measurements when compared to larger pressure-sensing devices, such as aortic pressure-sensing catheters.

Another method of measuring the pressure gradient across a lesion is to use a small catheter connected to a blood pressure sensor, which is often contained in a sensor housing associated with the catheter. However, this method can introduce error into the FFR measurement because as the catheter crosses the lesion, the catheter and the sensor housing themselves create additional blockage to blood flow across the lesion and contributes to a lower distal blood pressure than what would be caused by the lesion alone, which may exaggerate the measured pressure gradient across the lesion.

While the existing treatments have been generally adequate for their intended purposes, they have not been entirely satisfactory in all respects. The devices, systems, and associated methods of the present disclosure overcome one or more of the shortcomings of the prior art.

SUMMARY

In one exemplary embodiment, the present disclosure describes an apparatus for a micro-catheter having a sensor and a centering assembly to generally center the catheter within the vessel of interest. In one example, the sensor is a pressure sensor. In still a further aspect, the sensing micro-catheter has in internal lumen with a diameter large enough to receive a 0.014 inch diameter guidewire and an outside diameter of 0.035 inches or less.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTION OF THE DRAWINGS

The accompanying drawings illustrate embodiments of the devices and methods disclosed herein and together with the description, serve to explain the principles of the present disclosure.

DETAILED DESCRIPTION

Figure 1:
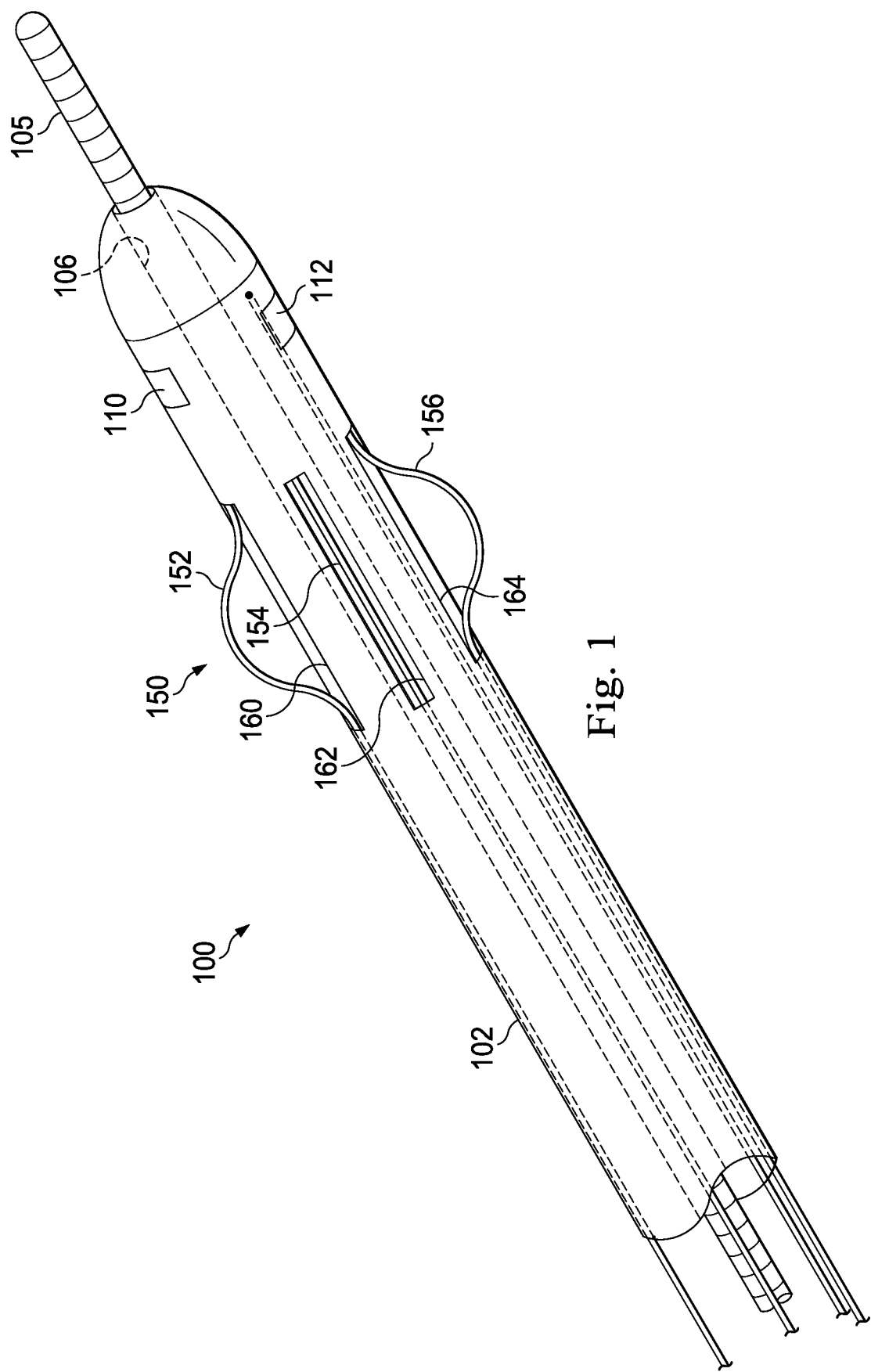
FIG. 1 is a diagrammatic partial perspective view of a sensing system according to one embodiment of the invention.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. For the sake of brevity, however, the numerous iterations of these combinations will not be described separately. For simplicity, in some instances the same reference numbers are used throughout the drawings to refer to the same or like parts.

The present disclosure relates generally to a device, systems, and methods of using a pressure-sensing catheter for the assessment of intravascular or intravenous pressure, including, by way of non-limiting example, the calculation of a FFR value. In some instances, embodiments of the present disclosure are configured to measure the pressure proximal to and distal to a stenotic lesion within a blood vessel. The pressure-sensing catheters disclosed herein enable the user to obtain pressure measurements using an existing guidewire (e.g., a conventional 0.014 inch guidewire) that can remain fairly stationary through the pressure measurement procedure. Thus, the pressure-sensing catheters disclosed herein enable the user to obtain physiologic information about an intravascular lesion upon pullback of the catheter without losing the original position of the guidewire. In addition, in one aspect, the sensing micro-catheter has an outer diameter of 0.035 inches or less such that conventional peripheral treatment devices may utilize the micro-catheter as a guiding member for positioning the treating device, such as a balloon, in the proper location. Still further, the treatment device may be deployed and withdrawn without moving the micro-catheter sensor such that the pressure can be sensed after treatment to determine effectiveness.

FIG. 1 illustrates a medical system 100 that is configured to measure pressure within a tubular structure V (e.g., a blood vessel) according to one embodiment of the present disclosure. In some embodiments, the medical system 100 is configured to calculate FFR based on the obtained pressure measurements. The system 100 includes a pressure-sensing micro-catheter 102 having two sensors 110 and 112 embedded in the distal portion thereof. FIG. 1 illustrates a pressure sensor 110 embedded in the catheter wall 102. Both for this embodiment and the other embodiments disclosed herein, the pressure sensor 110 comprises any type of pressure sensor that is sufficiently stress resistant to maintain functionality while embedded within the catheter wall. For example, the pressure sensor 110 may comprise a capacitive sensor, a piezoresistive pressure transducer, a fiber optic pressure sensor such as disclosed in U.S. Pat. Nos. 8,298, 156 and 8,485,985 and Application Nos. 2013/0303914 and 2013/0131523 (each incorporated by reference herein in their entirety), a sensor with a silicon backbone, or any other type of pressure sensor having the requisite durability and stress resistance. In some instances, the sensor 110 includes an array or plurality of sensor elements (e.g., a capacitive pressure sensor array). In the pictured embodiment, the sensor 110 includes a sensor diaphragm assembly. In some embodiments, the sensor diaphragm assembly includes a body having a recess covered by a flexible diaphragm configured to measure fluid pressure. The diaphragm may flex in response to variations in pressure around the diaphragm, thereby reflecting variations in blood pressure, for example. The sensor 110 can then measure and transmit the variations in pressure imparted on the diaphragm assembly. Still further, although the illustrated catheter is described in terms of a pressure sensor, it is contemplated that the type of sensing element disposed on the catheter is not a limitation with respect to all of the teachings of the present disclosure. More specifically, it is contemplated that while one sensor on the catheter may be a pressure sensor, an additional one or more imaging or flow sensors can be incorporated as the sensors of the present disclosure. For example, the sensors 110 and 112 could be ultrasonic transducers that can image the surrounding vessel such as by intravascular ultrasound (IVUS) and/or detect fluid flow in the vessel.

In the illustrated embodiment, the micro-catheter is formed with sensors 110 and 112 utilizing known techniques such as those found U.S. Pat. Nos. 6,030,371 and 7,776,380, each of which is incorporated by reference herein in their entirety. The catheter formation techniques can be utilized to form the channels, passages and electrical conductor members discussed below.

Figure 2:
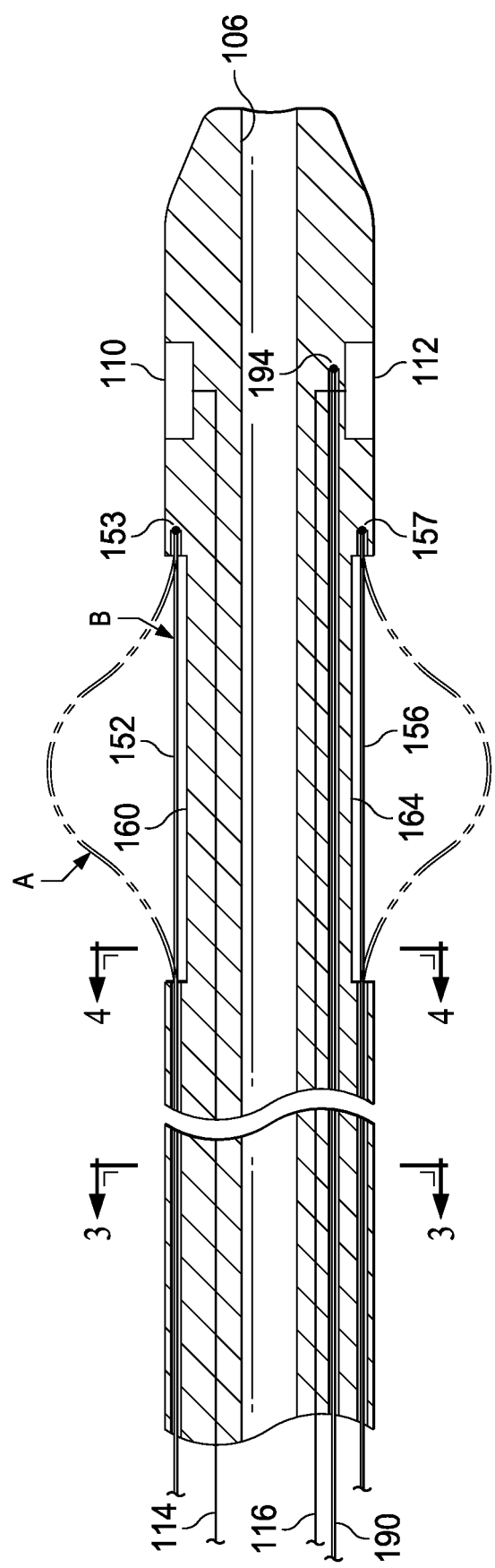
FIG. 2 is a diagrammatic partial cross-sectional side view of a micro-catheter sensing system according to an embodiment of the invention
Figure 4:
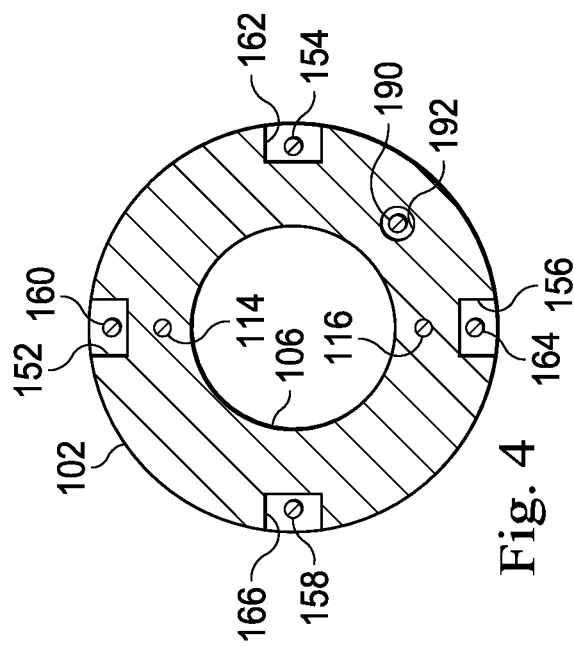
FIG. 4 illustrates a cross-section taken along lines 4-4 of FIG. 2.
Figure 3:
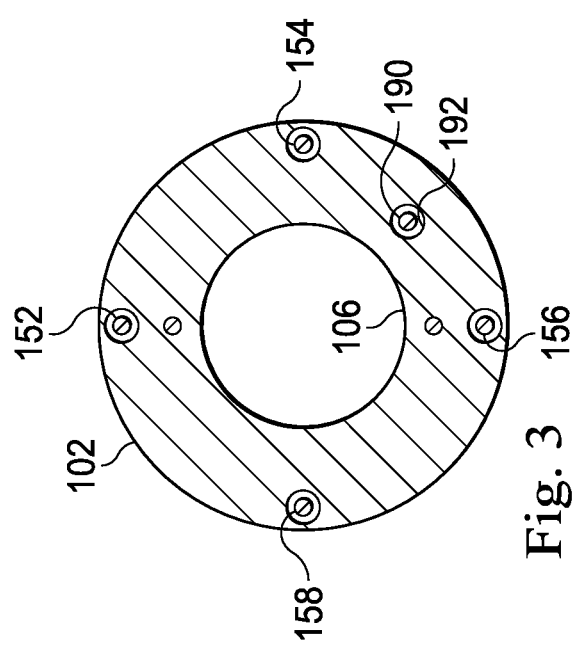
FIG. 3 illustrates a cross-section taken along lines 3-3 of FIG. 2.

Sensing micro-catheter 102 includes a centering assembly 150 that is configured to extend outwardly from the outer walls of the catheter to engage the surrounding vessel walls and move the sensors away from the vessel walls and into the primary flow of the vessel for more accurate sensor readings. With reference to FIGS. 1-4, the centering assembly includes four positioning wires 152, 154, 156 and 158 positioned uniformly around the circumference of the catheter 102. Each of the wires 152, 154, 156 and 158 extend through elongated channels 160, 162, 164 and 166 defined in the outer surface of the catheter body. The positioning wires are anchored in the distal end of the channels such as illustrated at locations 153 and 157 in FIG. 2. The positioning wires extend through and are slidable within tubular lumens (see FIG. 3) of the catheter 102. The positioning wires are joined to circular knob 210 (see FIG. 5) that slides linearly along the catheter body 102 within annular recess 220 to form a steering actuator 200. When knob 210 is moved in the direction of arrow C, the positioning wires are moved in the direction of arrow C until the deform outwardly adjacent the channels in the distal end of the catheter body in a centering configuration A as shown in FIGS. 1 and 2. When the knob is moved in the opposite direction, the positioning wires are withdrawn into the channels into an insertion configuration B as shown in FIG. 2.

In another aspect, the sensing catheter includes a steering mechanism 300 to permit the user to deflect the tip of the catheter to permit the catheter to be steered into the appropriate vessels or around obstructions. The steering mechanism includes a pull wire 190 anchored in the distal tip of the catheter body 102 at location 194 (FIG. 2). The pull wire 190 slidably extends within the catheter body 102 through a small lumen 192 to the proximal end of the catheter where the pull wire is joined to knob 310. Knob 310 is positioned in an annular recess 320 formed on the outside of the catheter body and can slide longitudinal along the catheter body. As the knob is moved forward and backward along the catheter body, the pull wire will act to deflect the distal tip of the catheter.

Sensors 110 and 112 are joined, via electrical conductors 114 and 116, to the proximal processing section 400. Processing section includes an application specific integrated circuit 410 configured to energize the sensors, receive sensor data, process the sensor data and provide outputs to the user through display 440 or through LED's 430. A battery 420 is also disposed within the catheter body 102 to power the ASIC, sensors, display and LED's. Either the display or the LED's can be used to provide battery charge information to the user. An RF coil or antenna 450 may be provided as means for external communication with other devices either to provide sensor output or receive control instruction, or both. Additionally, in some embodiments, the coil may be used for inductive coupling to charge battery 420 or otherwise power the sensors.

Figure 5:
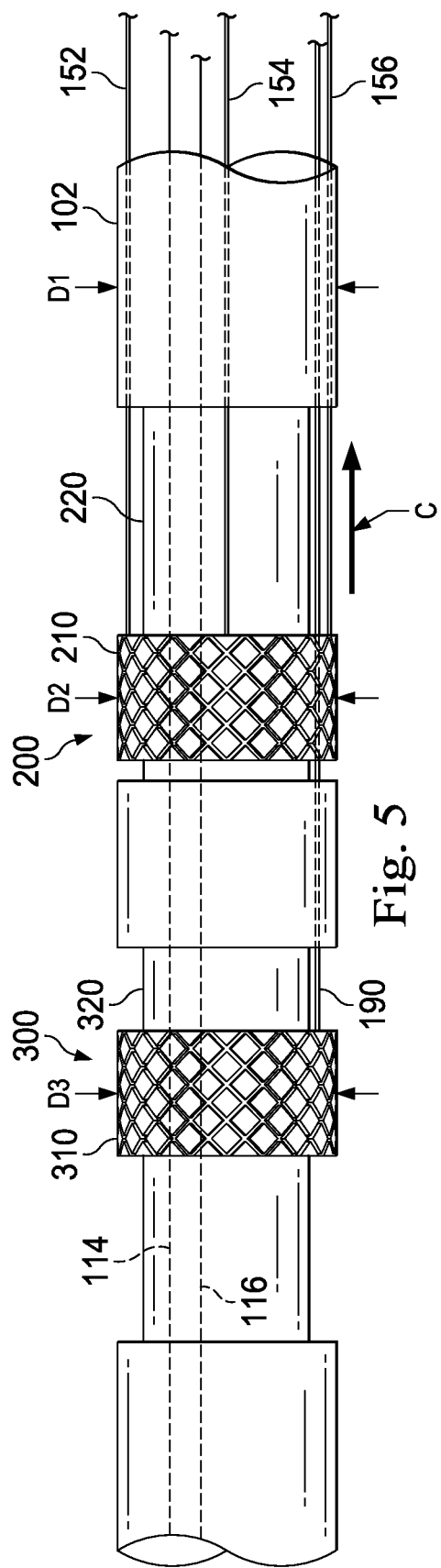
FIG. 5 is a partial side view of the proximal portion of the micro-catheter of FIG. 2.
Figure 6:
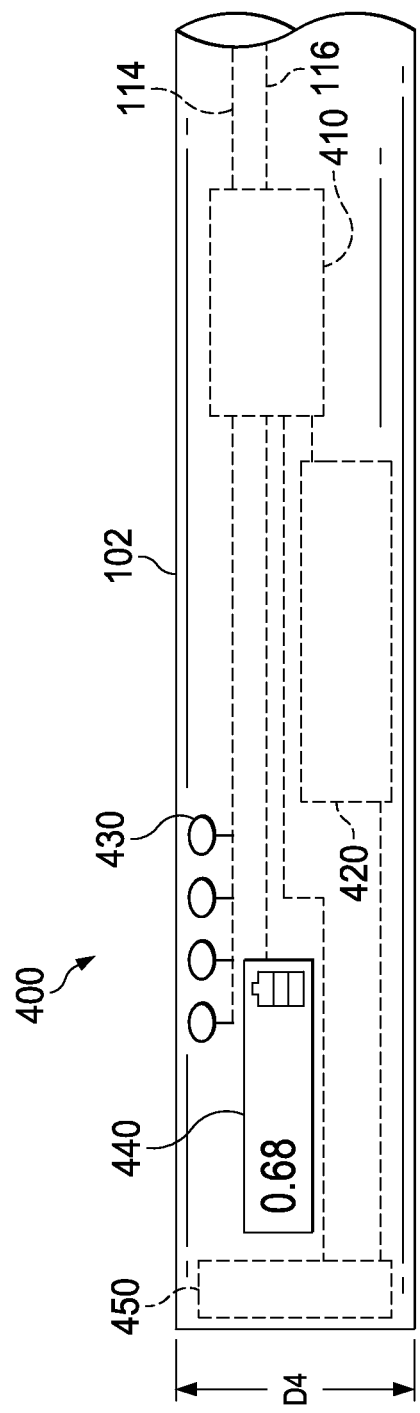
FIG. 6 is a partial side view of the proximal portion of the micro-catheter of FIG. 5.
Figure 7:
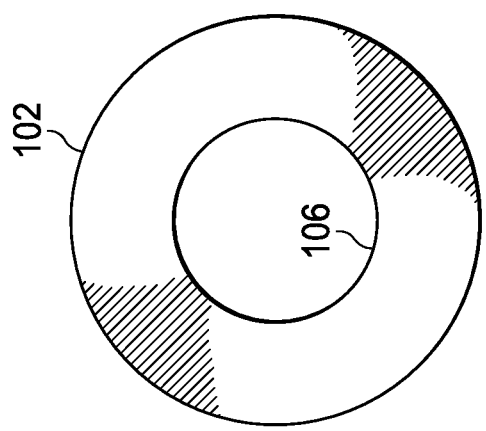
FIG. 7 is an end view of the micro-catheter of FIG. 6.

With reference to FIGS. 5, 6 and 7, the micro-catheter 102 has a generally uniform diameter D1 along its entire length. More specifically, the diameter D2 of the centering assembly actuator 210 is the same as D1. Likewise the diameter D3 of the steering actuator 310 is the same as D1 and the diameter of the proximal processing assembly D4 is the same as D1. Also, in the illustrated embodiment, the guidewire lumen 106 extends from the distal end to the proximal end. In one embodiment, the guidewire lumen 106 is sized to receive a guidewire 105 having an outer diameter of 0.014 inches and the maximum outer diameter of the micro-catheter 102 is no greater than 0.035 inches from the distal end to the proximal end.

In use, the guidewire 105 and micro-catheter 106 can be used to traverse a variety of obstacles within a patient. In one aspect, the micro-catheter 106 distal end is significantly more flexible than the guidewire 105. In one use to traverse a tortuous vessel or large curve, the guidewire is retracted about 10 cm within the micro-catheter and the steering assembly is actuated to curve the end of the micro-catheter. The catheter is the advanced along the curve into the desired position. Once in the desired position, the guidewire is advanced through the micro-catheter to stiffen the assembly. This process can be repeated to advance the assembly in the desired direction. In still a further aspect, the guide wire can have a stiff distal portion that can assist the assembly is passing through occlusions that would otherwise deflect the tip of the flexible micro-catheter. Once in the desired location, the sensors can be used to sense vessel characteristics such as pressure and flow of fluids within the vessel, or image the interior of the vessel. A treating device can be advanced over the micro-catheter, deployed to treat the vessel and then withdrawn. The sensors within the micro-catheter can again be utilized to sense the vessel characteristics to determine if the treatment was successful.

Figure 8:
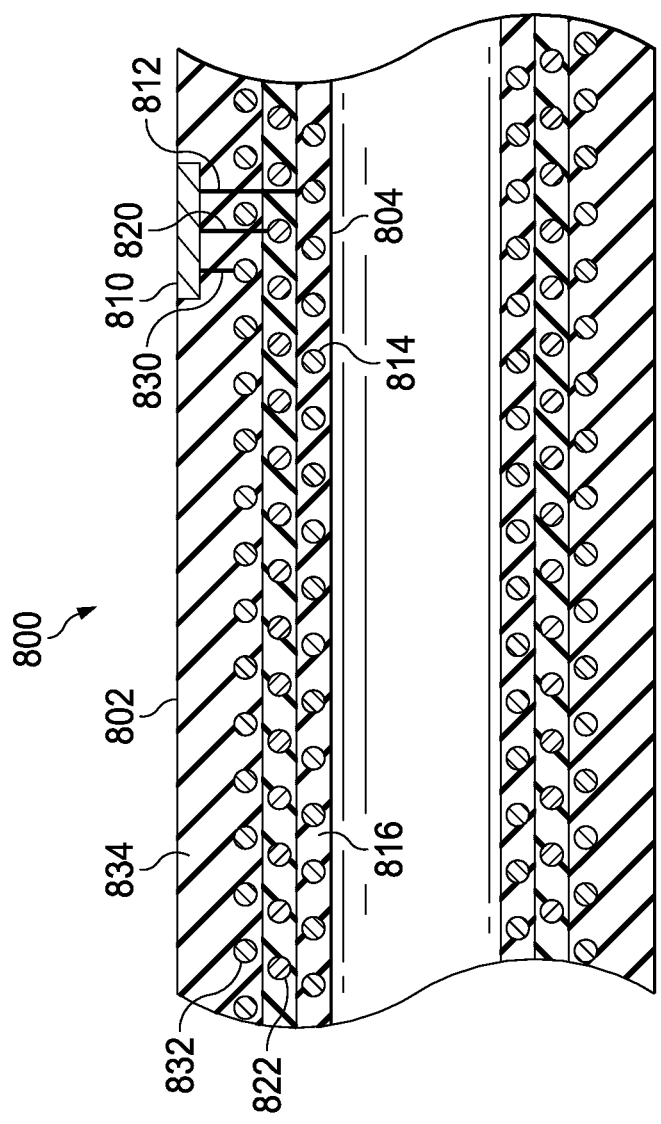
FIG. 8 is a partial cross-sectional view of a sensing micro-catheter according to another aspect of the present invention.

With reference now to FIG. 8, an alternative form of a sensing micro-catheter is illustrated. The micro-catheter 800 includes a sensor 810 and a series of reinforcing fiber layers surrounding an internal guidewire lumen 804. The sensor is electrically connected to the conductive reinforcing filaments 814 via conductor 812 and the filaments 814 are encapsulated by an insulating polymer. Similarly, conductor 820 connects the sensor to conductive filaments 822 which are encapsulated by a non-conductive polymer 824. Finally, conductor 830 connects sensor 810 to conductive filaments 832. The exterior of the catheter body is completed by coating with a non-conductive polymer layer 834. The resulting structure provides a fiber reinforced micro-catheter that has three electrically conductive bands extending the length of the catheter.

Persons of ordinary skill in the art will appreciate that the embodiments encompassed by the present disclosure are not limited to the particular exemplary embodiments described above. In that regard, although illustrative embodiments have been shown and described, a wide range of modification, change, and substitution is contemplated in the foregoing disclosure. For example, the pressure-sensing catheters disclosed herein may be utilized anywhere with a patient's body, including both arterial and venous vessels, having an indication for pressure measurement. It is understood that such variations may be made to the foregoing without departing from the scope of the present disclosure. Accordingly, it is appropriate that the appended claims be construed broadly and in a manner consistent with the present disclosure.

I claim:

1. An apparatus for intravascular pressure sensing, comprising:
    an elongate body having an outer surface, a proximal portion, and a distal portion, the elongate body being sized and shaped to be inserted into a vessel, the elongate body defining a lumen extending from the proximal portion to the distal portion of the elongate body, the lumen sized and shaped to allow the passage of a guidewire therethrough, the elongate body including two or more cylindrical layers extending from the lumen to the outer surface of the elongate body, wherein the two or more cylindrical layers comprise an inner cylindrical layer and an outermost cylindrical layer arranged around the inner cylindrical layer, wherein the elongate body includes a conductive filament arranged around the lumen and extending between the inner cylindrical layer and the outermost cylindrical layer from the distal portion of the elongate body to the proximal portion of the elongate body;
    a pressure sensor disposed within the outermost cylindrical layer of the two or more cylindrical layers at the distal portion of the elongate body; and
    an electronic component integrated within the elongate body at the proximal portion,
    wherein the conductive filament establishes electrical connection with the pressure sensor through the outermost cylindrical layer at the distal portion of the elongate body to transmit an electrical signal representative of a sensed pressure from the distal portion to the electronic component.

2. The apparatus of claim 1, further including a processing assembly disposed within the elongated body.

3. The apparatus of claim 1, wherein the lumen includes a diameter of 0.014 inches or greater.

4. The apparatus of claim 1, further including a steering mechanism to deflect a distal tip of the elongate body.

5. The apparatus of claim 4, further including a proximal centering actuator joined to a centering assembly and a proximal steering actuator joined to the steering mechanism.

6. The apparatus of claim 1, wherein the elongate body has an outer diameter of 0.035 inches or less for an entire length of the elongate body.

7. The apparatus of claim 1, wherein the conductive filament is connected to the pressure sensor via a conductor.

8. The apparatus of claim 1, wherein the conductive filament is encapsulated by an insulating polymer.

9. The apparatus of claim 8, wherein the encapsulated filament forms a cylindrical layer around the lumen.

10. The apparatus of claim 1, further comprising:
a centering assembly disposed adjacent to the pressure sensor, the centering assembly including a plurality of wires, each of the plurality of wires being positioned within one of a plurality of elongate channels defined in an outer surface of the elongate body, a distal end of each of the plurality of wires being anchored to a distal portion of one of the plurality of elongate channels, each of the plurality of wires extending proximally through and slidable within a tubular lumen in the elongate body, wherein the plurality of wires are outwardly deformable to engage a vessel wall.

11. The apparatus of claim 10, wherein the centering assembly is switchable between a first position where the plurality of wires are disposed within the plurality of elongate channels and a second position where a portion of each of the plurality of wires deforms outwardly from the plurality of elongate channels to engage a vessel wall to center the sensor within the vessel.

12. The apparatus of claim 11, wherein each of the plurality of wires includes a distal end and a proximal end and each of the plurality of elongate channels includes a distal portion, the distal end of each of the plurality of wires being anchored to the distal portion of one of the plurality of elongate channels.

13. The apparatus of claim 12, wherein the proximal ends of the plurality of wires are coupled to a knob, the knob being slidable along a longitudinal direction of the elongate body between a deployment position where the centering assembly is switched to the first position and a withdrawal position where the centering assembly is switched to the second position.

14. The apparatus of claim 1, wherein the conductive filament is electrically connected to the pressure sensor via a conductor extending through the outermost layer.

15. The apparatus of claim 1, wherein the conductive filament is a first conductive filament positioned within an intermediate cylindrical layer between the outermost cylindrical layer and the inner cylindrical layer, and wherein the elongate body further comprises a second conductive filament positioned within the outermost layer, wherein the first conductive filament and the second conductive filament establish electrical contact with the pressure sensor.

16. The apparatus of claim 15, wherein the elongate body further comprises a third conductive filament positioned within the inner cylindrical layer and establishing an electrical connection with the pressure sensor through the intermediate cylindrical layer and the outermost cylindrical layer.

17. A method, comprising
advancing a guidewire through a vessel to an area of interest;
positioning a sensing catheter over the guidewire, the sensing catheter including a sensor positioned adjacent a distal portion of the sensing catheter, a lumen, an electronic component integrated within a proximal portion of the sensing catheter, and wherein the sensing catheter includes two or more cylindrical layers comprising an inner cylindrical layer and an outermost cylindrical layer arranged around the inner cylindrical layer, wherein the sensing catheter includes a conductive filament arranged around the lumen and extending between the inner cylindrical layer and the outermost cylindrical layer from the distal portion of the sensing catheter to the electronic component, wherein the sensor is disposed within the outermost cylindrical layer at the distal portion of the sensing catheter, and wherein the conductive filament establishes electrical connection with the sensor through the outermost cylindrical layer at the distal portion of the sensing catheter;
advancing the sensing catheter over the guidewire to position the sensor in the area of interest;
sensing characteristics of the vessel in the area of interest;
transmitting data associated with the sensed characteristics of the vessel using the conductive filament from the sensor adjacent the distal portion to the electronic component; and
advancing a treating catheter over the sensing catheter to the area of interest.

18. The method of claim 17, wherein sensing characteristics includes sensing at least one of pressure, fluid flow or images.

19. The method of claim 17, wherein advancing the sensing catheter over the guidewire further includes positioning the sensing catheter and guidewire in a first position within a vessel, activating a catheter steering mechanism to deflect a tip of the sensing catheter and guidewire, advancing the guidewire to a second position within the vessel, and advancing the sensing catheter over the guidewire to the second position within the vessel.

20. The method of claim 17, further comprises:
prior to sensing characteristics of the vessel in the area of interest, centering the sensor within the vessel by deploying a centering assembly disposed adjacent the sensor, wherein the centering assembly includes a plurality of wires, each of the plurality of wires being positioned within one of a plurality of elongate channels around a circumference of the sensing catheter, wherein the plurality of wires are outwardly deformable to engage a vessel wall of the vessel.

21. The method of claim 17, wherein the proximal portion has a diameter identical to a diameter of the distal portion.

* * * * *